United States Patent [19]

Blade

[11] Patent Number: 5,380,732
[45] Date of Patent: Jan. 10, 1995

[54] PESTICIDAL COMPOUNDS

[75] Inventor: Robert J. Blade, Berkhamsted, England

[73] Assignee: Roussel-Uclaf, Paris, France

[21] Appl. No.: 960,275

[22] Filed: Oct. 13, 1992

Related U.S. Application Data

[63] Continuation of Ser. No. 362,203, Jun. 6, 1989, abandoned, which is a continuation-in-part of Ser. No. 355,975, May 22, 1989, abandoned.

[30] Foreign Application Priority Data

Nov. 28, 1986 [GB] United Kingdom ............... 8628467

[51] Int. Cl.$^6$ .................. C07D 213/64; A61K 31/505
[52] U.S. Cl. ................................... 514/351; 514/357; 546/300; 546/336
[58] Field of Search ............... 546/300, 336; 514/351, 514/357

[56] References Cited

FOREIGN PATENT DOCUMENTS

| | | |
|---|---|---|
| 0111105 | 6/1984 | European Pat. Off. . |
| 0164187A2 | 12/1985 | European Pat. Off. . |
| 0189936 | 8/1986 | European Pat. Off. . |
| 0269457A2 | 6/1988 | European Pat. Off. . |
| 57-212150 | 12/1982 | Japan . |
| 1215066 | 12/1970 | United Kingdom . |
| 1548033 | 7/1979 | United Kingdom . |
| 2101600 | 1/1983 | United Kingdom . |

*Primary Examiner*—Robert Gerstl
*Attorney, Agent, or Firm*—Nixon & Vanderhye

[57] ABSTRACT

A compound of Formula I or a salt thereof:

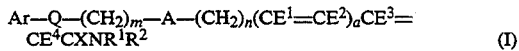

$$Ar-Q-(CH_2)_m-A-(CH_2)_n(CE^1=CE^2)_aCE^3=CE^4CXNR^1R^2 \quad (I)$$

where Ar is a 6-membered heteroaromatic ring containing, as the heteroatom or heteroatoms, one or two nitrogen atoms and is optionally substituted by one or more of halogen, cyano, $C_{1-6}$-alkyl (optionally substituted by halogen), or $C_{1-6}$- alkoxy (optionally substituted by one or more of halogen or $C_{1-6}$-alkyl), or $RS(O)_x$ where x is 0, 1 or 2 and R is $C_{1-6}$-alkyl optionally substituted by one or more halogen atoms, Q is —$CH_2$— or —O—, m and n are each independently 0 to 7, A is —$CH_2$— or —O—, a is 0 or 1, $E^1$ to $E^4$ are independently hydrogen, $C_{1-4}$-alkyl or halo-$C_{1-4}$-alkyl or halogen, X is oxygen or sulphur, and $R^1$ and $R^2$ are independently hydrogen, $C_{1-6}$ alkyl or $C_{3-6}$-cycloalkyl, either being optionally substituted by one or more of $C_{1-6}$-alkyl, $C_{2-6}$-alkenyl, dioxalanyl, $C_{3-6}$-cycloalkyl, $C_{1-6}$-alkoxy or $RS(O)_x$ as defined above.

The compounds and their salts are useful as insecticides and acaricides.

14 Claims, No Drawings

PESTICIDAL COMPOUNDS

This is a continuation of application Ser. No. 07/362,203, filed Jun. 6, 1989, now abandoned which is a continuation-in-part of U.S. Ser. No. 07/355,975, filed May 22, 1989 now abandoned.

The present invention relates to pesticidal lipid amide compounds.

EP-A-164 187 discloses a range of largely w-benzyloxy or phenoxy ether-linked lipid amide compounds as being pesticidal.

JP-A-57 212 150 discloses certain w-phenoxy and w-benzyl lipid amides as insecticides and miticides.

It has now been found that compounds having an w-heterocyclic 6-membered aromatic ring show useful levels of pesticidal activity.

Accordingly, one aspect of the present invention provides compounds of Formula I or salts thereof:

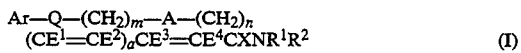
(I)

where Ar is a 6-membered heteroaromatic ring containing, as the heteroatom or heteroatoms, one or two nitrogen atoms and is optionally substituted by one or more of halogen, cyano, $C_{1-6}$-alkyl (optionally substituted by one or more halogen atoms), $C_{1-6}$- alkoxy (optionally substituted by one or more of halogen or $C_{1-6}$-alkyl), or $RS(O)_x$- where X is 0, 1 or 2 and R is $C_{1-6}$-alkyl optionally substituted by one or more halogen atoms, Q is —CH$_2$— or —O—, m and n are each independently 0 to 7, A is —CH$_2$— or —O—, a is 0 or 1, E$^1$ to E$^4$ are independently hydrogen, $C_{1-4}$-alkyl, halo-$C_{1-4}$-alkyl or halogen, X is oxygen or sulphur, and R$^1$ and R$^2$ are independently hydrogen, $C_{1-6}$ alkyl or $C_{3-6}$-cycloalkyl, either being optionally substituted by one or more of $C_{1-6}$-alkyl, $C_{2-6}$-alkenyl, dioxalanyl, $C_{3-6}$-cycloalkyl, $C_{1-6}$-alkoxy or $RS(O)_x$ as defined above.

Ar may, for example, be pyridine, pyrazine, pyrimidine or pyridazine and may be attached to the lipid chain at any of the possible positions on the Ar ring. Preferably, Ar is optionally substituted 2-pyridyl or 4-pyridyl, any substitution being preferably, in the latter case, in the 2'- or 5'-position and, in the former case, in the 3'-, 5'-, 6'-, 3',6', 4', 6' or 5',6'-positions. Preferred substituents are halo (such as chloro or bromo), trifluoromethyl or trifluoromethylthio (or oxides thereof).

Preferably, Q is —O—. Suitably, X is oxygen.

Preferably, A is —CH$_2$— and the sum of m and n is even, such as 4, 6 or 8, most preferably 6.

Suitably, a is 1. Advantageously the or each double bond conjugated to the carbonyl is trans.

Conveniently, E$^1$ if present, is hydrogen, E$^3$ is hydrogen or methyl and E$^2$ and E$^4$ are hydrogen or fluoro.

Preferably, R$^1$ is hydrogen and R$^2$ is $C_{1-8}$ alkyl (such as isobutyl, 1,2-dimethylpropyl, 2,2-dimethylpropyl, 1-methylpropyl or 1,1,2-trimethylpropyl), dioxalanylalkyl (such as (2-methyl-1,3-dioxalan-2-yl) methyl) or alkenyl (such as 2-methyl-prop-2-enyl).

Particularly preferred compounds include (2E,4E)N-isobutyl 12-(6-chloro-2'-pyridyloxy)dodeca-2,4-dienamide; (2E,4E)N-isobutyl 3-methyl-12-(6'-trifluoromethyl -2'-pyridyloxy)3-methyldodeca-2,4-dienamide; (2E,4E) N-isobutyl 12-(4',6'-bistrifluoromethyl-2'-pyridyloxy) -dodeca-2,4-dienamide; (2E,4E) N-(2-methyl-1,3-dioxalan -2- yl)-methyl 12-(4',6'-bistrifluoromethyl -2-pyridyloxy)- dodeca-2,4-dienamide; (2Z,4E)N-Isobutyl 2-fluoro -3-methyl-12-(3-chloro-5-trifluoromethyl-2-pyridyloxy)dodeca-2, 4-dienamide; (2Z,4E)N-Isobutyl 2-fluoro-3-methyl-12-(3,5-bistrifluoromethyl -2-pyridyloxy)dodeca-2,4-dienamide.

Compounds of Formula (I) may be prepared in any of the following ways:

(a) when X is oxygen, by amidation of the corresponding acid or acid derivative, i.e. by reaction of a compound of Formula (II) with a compound of Formula (III):

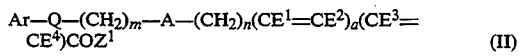
(II)

(III)

where Z$^1$ is hydroxy, alkoxy, halo or a phosphoroimidate ester group and the other variables are as defined above;

(b) by reaction of a compound of Formula (IV) with a compound of Formula (V):

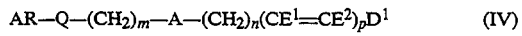
(IV)

(V)

wherein one of D$^1$ and D$^2$ is an aldehyde group —CHO and the other is a group $(Z^2)_3P$=CH— or $(Z^2)_2P(\rightarrow O)$=CH—, where Z$^2$ is alkyl, alkoxy preferably ethoxy) or aryl (preferably phenyl), one of p and q is 0 and the other is 1 or 0;

(c) by β-elimination from a compound of Formula (VI) or (VII):

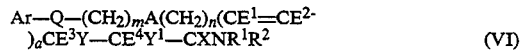
(VI)

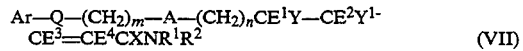
(VII)

wherein one of Y and Y$^1$ is hydrogen and the other is a leaving group D(→O)L, where D is sulphur or selenium and L is a suitable group such as lower alkyl (preferably methyl) or aryl (preferably phenyl);

(d) when X is oxygen, by reaction of a compound of Formula (VIII) with a compound of Formula (IX):

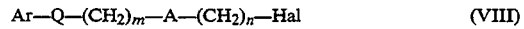
(VIII)

(IX)

wherein Hal is a halogen atom, and G is a group HC≡C—(CE$^3$=CE$^4$)— or a group HC≡C—, followed by reduction of the triple bond, for example by hydrogenation;

(e) when a=1, by reaction of a compound of Formula (X) with a compound of Formula (XI)

(X)

(XI)

wherein Hal is halide (e.g. bromide or iodide) and M$^1$ is a metal-containing group, for example comprising zirconium, aluminium or zinc, e.g. a bis-(cyclopentadienyl)zirconium chloride group;

(f) when A is —O—, by reaction of a compound of Formula (XII) with a compound of Formula (XIII):

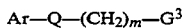 Ar—Q—(CH$_2$)$_m$—G$^3$ (XII)

G$^4$—(CH$_2$)$_n$(CE$^1$=CE$^2$)$_a$(CE$^3$=CE$^4$) CXNR$^1$R$^2$ (XIII)

wherein one of G$^3$ and G$^4$ is hydroxy or a suitable leaving group such as halo and the other is —OH, —OM or —M where M is a suitable metal such as sodium or lithium.

(g) when X is sulphur, by reaction of a compound of Formula (XX) with phosphorus pentasulphide (P$_2$S$_5$), hydrogen sulphide, boron trisulphide, thiophosphoryl bromide or a compound of Formula (XXI):

Ar—Q—(CH$_2$)$_m$—A—(CH$_2$)$_n$—(CE$^1$=CE$^2$-)$_a$CE$^3$=CE$^4$CONR$^1$R$^2$ (XX)

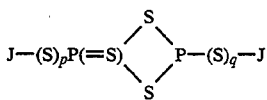

J—(S)$_p$P(=S)⟨S/S⟩P—(S)$_q$—J (XXI)

where p and q are each independently 0 is 1 and J is a suitable aromatic group; or (h) when R is hydrogen and X is sulphur, by reaction of a compound of Formula (XXII) with a compound of Formula (XXIII):

Ar—Q—(CH$_2$)$_m$—A—(CH$_2$)$_n$—(CE$^1$=CE$^2$-)$_a$CE$^3$=CE$^4$—M$^2$ (XXII)

SCNR$^3$ (XXIII)

where M$^2$ is a metal atom, preferably magnesium, lithium, aluminium or zirconium, or a functional group containing one of those said metal atoms.

Process (a) is normally carried out in an aprotic solvent such as dichloromethane, ether or toluene, optionally in the presence of a tertiary amine such as triethylamine or in the presence of trimethylaluminium (when Z$^1$ is alkoxy), but in the absence of water. If the compound of Formula (II) is an acid halide, for example acid chloride, then it may be formed from the corresponding acid by reaction with a suitable reagent such as oxalyl chloride or thionyl chloride. When Z$^1$ is a phosphoroimidate group then this is suitably formed from PhOP(O)(NHPh)Cl. The acid function in the compound of Formula (II) may be prepared by hydrolysis of an ester, the ester being prepared by a conventional Wittig or Wadsworth-Emmons reaction, using for example an aldehyde and ethoxycarbonylmethylene triphenylphosphorane or the anion from a triethylphosphonocrotonate.

The ester of Formula (II) may be derived by rearrangement and elimination reaction analogous to that of step (c) above using a suitable ester, such as a simple alkyl ester. The starting ester for such a reaction may be obtained by reaction of a compound of Formula (XIV) with a compound of Formula (XV):

Ar—Q—(CH$_2$)$_m$—A—(CH$_2$)$_n+2$CHO (XIV)

PhS(→O)CH$_2$COO—Alkyl (XV)

or by analogous reactions.

A further route is for the ester of Formula (II) to be prepared by elimination on a compound of Formula (XVI):

Ar—Q—(CH$_2$)$_m$—A—(CH$_2$)$_n$—A$^1$—A$^2$—A$^3$—COO—Alkyl (XVI)

wherein one of A$^1$, A$^2$ and A$^3$ is (CE=CE)$_a$, another of A$^1$, A$^2$ and A$^3$ is CE$_2$-, and the third of A$^1$, A$^2$ and A$^3$ is CE(OR$^3$)-, R$^3$ being H or acyl (such as acetyl), and the said —CEH— and —CE(OR$^3$)— groups are adjacent one another, where each E is hydrogen or one of E$^1$ to E$^4$ as appropriate. The reaction is preferably carried out in an aromatic solvent, conveniently in the presence of a molybdenum catalyst and a base, such as bistrimethyl silylacetamide. Intermediates of Formula (XVI) may be obtained by reaction of a suitable aldehyde with a suitable sulphinyl compound, followed by acylation.

Process (b) is suitably carried out in a dry solvent, for example tetrahydrofuran (THF), optionally in the presence of a base, and preferably under nitrogen at a low temperature. The Wittig-type reagent of Formula (IV) or (V) may be obtained with lithium diisopropylamide.

Process (c) is normally carried out by heating in an aprotic solvent such as benzene or toluene, preferably in the presence of an acid catalyst, such as paratoluenesulphonic acid. Process (d) preferably proceeds by reaction of the compound of Formula (IX) with a base (such as lithium diisopropylamide) and the compound of Formula (VIII) in an aprotic solvent such as THF. Process (e) is conveniently carried out in an aprotic solvent such as THF, under an inert atmosphere (such as argon) and in the presence of a palladium (O) catalyst, such as bis (triphenylphosphine) palladium. When process (f) comprises the reaction of two alcohols, a dehydrating agent such as concentrated sulphuric acid or diethyldiazocarboxylate is preferably present. When G$^3$ or G$^4$ is halo, a base is preferably present. Other standard methods for making ethers are to be found in the "Compendium of Organic Synthetic Methods", Harrison and Harrison, Wiley Interscience, 1971.

Process (g) is preferably performed in an aromatic solvent such a toluene or xylene. Process (h) is preferably performed in an anhydrous inert solvent such as an ether (e.g. tetrahydrofuran) in the absence of oxygen (e.g. under a nitrogen atmosphere).

Furthermore, the intermediates of Formulae (II) to (XXIII) may in general be prepared by standard methods. For example, compounds of Formula (V) may be prepared by the reaction of an appropriate phosphine, phosphonate or phosphite with an w-halo amide.

The carbonyl-containing compounds of Formula (IV) may be prepared, for example, by hydrolysis of a ketal or acetal ring or oxidation of an alcohol (XVII), for example using pyridinium chlorochomate or oxalyl chloride/dimethyl sulphoxide.

Compounds of Formula (XVII):

Ar Q(CH$_2$)$_m$A(CH$_2$)$_n+1$OH (XVII)

may be prepared by reaction of a compound of Formula (XVIII) with one of Formula (XIX) wherein Q is —O—:

X$^2$—(CH$_2$)$_m$A(CH$_2$)$_n+1$OH (XVIII)

Ar-Y$^2$ (XIX)

where one of $X^2$ and $Y^2$ is OH and the other is OH or halogen. This process may be carried out in the presence of a metal, for example sodium, in an aprotic solvent, for example toluene or dimethylformamide.

The compounds of Formula (I) and their acid addition salts may be used to control pests such as arthropods, e.g. insect and acarine pests. Thus, the present invention provides a method for the control of arthropods which comprises administering to the arthropod or to its environment an arthropodicidally effective amount of a compound of the Formula (I). The present invention provides a method for the control of arthropod infestations of animals (including humans) and/or or plants (including trees) and/or stored products which comprises administering an effective amount of a compound of the Formula (I). The present invention further provides for the compounds of the Formula (I) for use in human and veterinary medicine, in public health control and in agriculture for the control of arthropod pests. By "control of pests" we mean the amelioration of present or future deleterious effects of pests, including killing adults, larvae and eggs, repelling pests, knocking down pests, inhibiting reproduction of pests and other influence on the behaviour of pests.

The compounds of Formula (I) are of particular value in the protection of field, forage, plantation, glasshouse, orchard and vineyard crops, of ornamentals and of plantation and forest trees, for example cereals (such as maize, wheat, rice, millet, oats, barley and sorghum), cotton, tobacco, vegetables and salads (such as beans, cole crops, cucurbits, lettuce, onions, tomatoes and peppers), field crops (such as potato, sugar beet, ground nuts, soyabean, oil seed rape), sugar cane, grassland (including playing fields) and forage crops, (such as lucerne), plantations (such as of tea, coffee, cocoa, banana, oil palm, coconut, rubber, spices), orchards and groves (such as of stone and pip fruit, citrus fruits, kiwifruit, avocado, mango, olives and walnuts), vineyards, ornamental plants, flowers and shrubs under glass and in gardens and parks, forest trees (both deciduous and evergreen) in forests, plantations and nurseries, and plants grown for industrial or pharmaceutical purposes (such as the evening primrose).

They are also valuable in the protection of timber (standing, felled, converted, stored or structural) from attach by sawflies (e.g. Urocerus) or beetles (e.g. scolytids, platypodids, lyctids, bostrychids, cerambycids, anobiids).

They have applications in the protection of stored products such as grains, fruits, nuts, spices and tobacco, whether whole, milled or compounded into products, from moth, beetle and mite attack. Also protected are stored animal products such as skins, hair, wool and feathers in natural or converted form (e.g. as carpets or textiles) from moth and beetle attack; also stored meat and fish from beetle, mite and fly attack.

Compounds of Formula (I) are of value in the control of arthropods which are injurious to, or spread or act as vectors of diseases in, man and domestic animals, for example those hereinbefore mentioned, and more especially in the control of ticks, mites, lice, fleas, midges, biting, nuisance and myiasis flies, and mosquitoes.

Compounds of Formula (I) are of value in the control of public health pests such as hemipteran bugs, cockroaches and ants.

Compounds of Formula (I) may be used for such purposes by application of the compounds themselves or in diluted form in known fashion as a dip, spray, fog, lacquer, foam, dust, powder, aqueous suspension, paste, gel, cream, shampoo, grease, combustible solid, vapourising mat, combustible coil, bait, dietary supplement, wettable powder, granule, aerosol, emulsifiable concentrate, oil suspension, oil solution, pressure-pack, impregnated article, microcapsule, pour on formulation or other standard formulations well known to those skilled in the art. Sprays may be applied by hand or by means of a spray race or arch or vehicle- or aircraft-mounted apparatus. The animal, soil, plant or other surface being treated may be saturated with the spray by means of high volume application or superficially coated with the spray by means of light or ultra low volume application. Dip concentrates are not applied per se, but diluted with water and the animals immersed in a dipping bath containing the dip wash. Sprays may be applied by hand or by means of a spray race or arch. The animal, plant or surface may be saturated with the spray by means of high volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material, such as that against which animals rub and transfer the material to their skins. Pour-on formulations are dispensed as a unit of liquid of small volume on to the backs of animals such that all or most of the liquid is retained on the animals.

The compounds of Formula (I) may be prepared either as formulations ready for use on the animals, plants or surface or as formulations requiring dilution prior to application, but both types of formulation comprise a compound of Formula (I) in intimate admixture with one or more carries or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powder and granules and other solid formulations comprise the compound of Formula (I) in intimate admixture with a powdered solid inert carrier for example suitable clays, kaolin, bentonite, attapulgite, adsorbent carbon black, talc, mica, chalk, gypsum, tricalcium phosphate, powdered cork, magnesium silicate, silicon dioxide, vegetable carriers, starch and diatomaceous earths. Such solid formulations are generally prepared by impregnating the solid diluents with solutions of the compound of Formula (I) in volatile solvents, evaporating the solvents and, if desired, grinding the products so as to obtain powders and, if desired, granulating, compacting or encapsulating the products.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil), which may also be used for dipping purposes. The concentrate preferably comprises a mixture of the active ingredient, with or without an organic solvent and one or more emulsifiers. Solvents may be present within wide limits but preferably in an amount of from 0 to 99.9% w/v of the composition and may be selected from water, mineral oil, kerosene, ketones, alcohols, xylene, aromatic naphtha, aromatic and aliphatic esters and other solvents known in the formulating art. The concentration of emulsifiers may be varied within wide limits but is preferably in the range of 1 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates soaps, lecithins or hydrolysed glues etc.

Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 0.5 to 99.5% by weight of the active ingredient, and are diluted, for example with water, before use.

Lacquers comprise a solution of the active ingredient in an organic solvent together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as a uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes, butane, propane, dimethyl ether and the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body. Suitably the plastics material is a polyvinyl chloride (PVC).

The concentration of the compound of Formula (I) to be applied to an animal, premises, other substrates or outdoor areas will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited will vary according to the method of application, area of application, concentration of the compound in the applied formulation, factor by which the formulation is diluted, the efficacy of the compound and the nature of the formulation. Undiluted formulations such as pour-on formulations will in general be deposited at a concentration in the range from 0.1 to 20.0% and preferably 0.1 to 10%. The amount of compound to be applied to stored products in general will lie in the range of from 0.1 to 20 ppm.w/w. Space sprays will be applied to give an average initial aerial concentration of 0.001 to 1 mg/m$^3$.

The compounds of Formula (I) are also of use in the protection and treatment of plant species, in which case an effective insecticidal, acaricidal or nematocidal amount of the active ingredient is applied. The application rate will vary according to the compound chosen, the nature of the formulation, the mode of application, the plant species, the planting density and likely infestation and other like factors but in general, a suitable use rate for agricultural crops is in the range 0.001 to 3 kg/Ha and preferably between 0.01 and 1 kg/Ha. Typical formulations for agricultural use contain betwen 0.0001% and 50% of a compound of Formula (I) and conveniently betwen 0.1 and 15% by weight of a compound of the Formula (I).

Dusts, greases, pastes and aerosol formulations are usually applied in a random fashion as described above and concentrations of 0.001 to 20% w/v of a compound Formula (I) in the applied formulation may be used.

The compounds of Formula (I) have been found to have activity against the common housefly (*Musca domestica*). In addition, certain compounds of Formula (I) have activity against other arthropod pests including *Myzus persicae, Tetranychus urticae, Plutella xylostella,* Culex spp. *Tribolium castaneum, Sitophilus granarius, Periplaneta americana* and *Blattela germanica.* The compounds of Formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. Anobium, Ceutorhynchus, Rhynchophorus, Cospopolites, Lissorhoptrus, Meligethes, Hypothenemus, Hylesinus, Acalymma, Lema, Psylliodes, Leptinotarsa, Gonocephalum, Agriotes, Dermolepida, Heteronychus, Phaedon, Tribolium, Sitophilus, Diabrotica, Anthonomus or Anthrenus spp.), Lepidoptera e.g. Ephestia, Mamestra, Earias, Pectinophora, Ostrinia, Trichoplusia, Pieris, Laphygma, Agrotis, Amathes, Wiseana, Tryporyza, Diatraea, Sporganothis, Cydia, Archips, Plutella, Chilo, Heliothis, Spodoptera or Tineola ssp.), Diptera (e.g. Musca, Aedes, Anopheles, Culex, Glossina, Simulium, Stomoxys, Haematobia, Tabanus, Hydrotaea, Lucilia, Chrysomia, Callitroga, Dermatobia, Gasterophilus, Hypoderma, Hylemyia, Atherigona, Chlorops, Phytomyza, Ceratitis, Liriomyza, and Melophagus spp.), Phthiraptera, Malophaga e.g. Damalinia spp. and Anoplura e.g. Linognathus and Haematopinus spp.), Hemiptera (e.g. Aphis, Bemisia, Phorodon, Aeneoplamia, Empoasca, Parkinsiella, Pyrilla, Aonidiella, Coccus, Pseudococcus, Helopeltis, Lygus, Dysdercus, Oxycarenus, Nezara, Aleurodes, Triatoma, Rhodnius, Psylla, Myzus, Megoura, Phylloxera, Adelyes, Niloparvata, Nephrotettix or Cimex spp.), Orthoptera (e.g. Locusta, Gryllus, Schistocerca or Acheta spp.), Dictyoptera (e.g. Blattella, Periplaneta or Blatta spp.), Hymenoptera (e.g. Athalia, Cephus, Atta, Lasius, Solenopsis or Monomorium spp.), Isoptera (e.g. Odontotermes and Reticulitermes spp.), Siphonaptera (e.g. Ctenocephalides or Pulex spp.), Thysanura (e.g. Lepisma spp.), Dermaptera (e.g. Forficula spp.) and Psocoptera (e.g. Peripsocus spp.) and Thysanoptera (e.g. *Thrips tabaci*).

Acarine pests include ticks, e.g. members of the genera Boophilus, Ornithodorus, Rhipicephalus, Amblyomma, Hyalomma, Ixodes, Haemaphysalis, Dermocentor and Anocentor, and mites and manges such as Acarus, Tetranychus, Psoroptes, Notoednes, Sarcoptes, Psorergates, Chorioptes, Demodex, Panonychus, Bryobia and Eriophyes spp.

Compounds of the invention may be combined with one or more other pesticidally active ingredients (for example pyrethroids, carbamates, lipid amides, bicyclooctanes and organophosphates) and/or with attractants, repellents, bacteriocides, fungicides, anthelmintics and the like. Furthermore, the activity of the compounds of the invention may be enhanced by the addition of a synergist or potentiator, for example one of the oxidase inhibitor class of synergists (such as piperonyl butoxide) or propyl 2-propynylphenylphosphonate, or a pyrethroid pesticidal compound. When an oxidase inhibitor synergist is present in a formulation of the invention, the ratio of synergist to compound of Formula (I) will be in the range 500:1–1:25 e.g. about 100:1 to 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin) and organic or inorganic bases e.g. trialkylamines such as triethylamine which can act as basic stabilisers and as scavengers.

Buffers may be used to control the pH of the formulations.

It will be understood that what we will claim may comprise:
(a) compounds of Formula (I) and their salts;
(b) processes for the preparation of compounds of Formula (I) and their salts;
(c) insecticidal and acaricidal compositions comprising a compound of Formula (I) or a salt thereof in admixture with a carrier:
(d) processes for the preparation of such pesticidal compositions;
(e) methods for the control of insect or acarine pests comprising the application to the pest or its environment of a compound of Formula (I) or a salt thereof;
(f) synergised pesticidal compositions comprising a compound of Formula (I) or a salt thereof; and
(g) potentiating or non-potentiating mixtures of a compound of Formula (I) or a salt thereof and another pesticidal compound;
(h) novel intermediates in the preparation of compounds of Formula (I), particularly compounds of Formula (II).

The following Examples illustrate, in a non-limiting manner, preferred aspects of the invention. All temperatures are in degrees Celsius. Unless otherwise indicated, all dienamides are of the (2E,4E) configuration, except that those having a 3-methyl substituent are (2E/Z,4E), with the (2E,4E) configuration predominating.

EXAMPLE 1

N-Isobutyl 12-(6'-chloro-2'-pyridyloxy)dodeca-2,4-dienamide 1,8-Octanediol (14.62 g, 0.1 mole) was dissolved in benzene (200 mls) and 12.5 mls of conc (46.48%) aqueous HBr added. The mixture was then heated overnight at reflux whilst removing the water using a Dean & Stark apparatus. About 12 mls of water were rapidly removed within the first 4 hours. The crude mixture was washed with 6N NaOH (100 mls), 10% aq HCl (100 mls), water (2×200 mls) and brine (150 mls). The solvent was removed to give a colourless liquid, (14.8 g, 71%) 1-bromooctan-8-ol.

Ref: Synthesis, 1985, 1161.

6-Chloro-6-hydroxypyridine (Aldrich) (1.94 g, 15 mmol) in dry dimethylformamide (DMF) (3 ml) was added to a suspension of hexane washed sodium hydride (18 mmol) in dry DMF (11 ml). After stirring at room temperature for 2 hours, 8-bromo-octan-1-ol (3.15 g) was added. The mixture was warmed at 60° for 2 hours and left at room temperature for 16 hours. After conventional work-up and chromatography on silica, 8-(6'-chloro-2-pyridyl)oxyoctan-1-ol was obtained.

The above alcohol (3.46 g, 13.4 mmol) was added to a complex prepared from oxalyl chloride (1.29 ml) and dimethyl sulphoxide (2.10 ml) in dry dichloromethane at −60° under nitrogen. After 0.5 hours triethylamine (5 equiv.) was added and the reaction mixture was allowed to reach room temperature and worked up in the usual manner to give 8-(6-chloro-2-pyridyl)oxy-octan-1-al.

A solution of lithium diisopropylamide in dry tetrahydrofuran (THF) was prepared from n-butyl lithium (4.52 mmol) and diisopropylamine (4.74 mmol). Triethylphosphonocrotonate (4.52 mmol) in THF was added at −60° and the mixture allowed to reach −10° whereupon it was cooled and the above aldehyde (1.1 g, 4.31 mmol) in THF was added at −40°. After stirring under $N_2$ at room temperature for 18 hours, the mixture was worked up in the standard fashion to give ethyl 12-(6'-chloro-2'-pyridyloxy)-deca-2,4-dienoate.

The above ester (0.57 g, 1.62 mmol) was added at −10°, under dry nitrogen, to from a complex prepared from trimethyl aluminium (2M in toluene, 1.78 mmol) and isobutylamine (0.193 mls, 1.95 mmol). The whole was heated under reflux for 2 hours, allowed to cool and worked up in normal fashion. Chromatography on silica with ether-hexane as eluant gave N-isobutyl 12-(6'- chloro-2-pyridyloxy)-deca-2,4-dienamide as a mixture of (2E,4E) and (2E,4Z) isomers.

EXAMPLE 2

(2E,4E) N-Isobutyl 12-(6-chloro-2-pyridyloxy) dodeca-2,4-dienamide

The mixture of isomers from Example 1 was subjected to further chromatography and recrystallisation from ether-hexane to give (2E,4E) N-isobutyl 12-(6'chloro-pyridyloxy)dodeca -2,4-dienamide m.p. 80°-1°, NMR 7.53 ( 1H), d of d, 6.89 (1H), d, 6.63 (1H), d, pyridyl; 7.2 ( 1H), H3; 6.1 (2H), m, H4,5; 5.75 (1H), d, H2; 5.49 ( 1H), NH; 4.28 (2H), t, H12; 2.15.(2H), m, H6; 1.87–1.15 ( 10H) m, H7–11 inc: 3.18 (2H), d of d, 1.6 (1H), m, 0.91 ( 6H), d, isobutyl. Mass spec: m+1, 379, 381.

EXAMPLE 3

(2E,4E) N-isobutyl 12-(6trifluoromethyl-2'-pyridyloxy)dodeca-2,4-dienamide

To a suspension of 1,8-octandiol (16.8 g) in dry toluene (80 ml) was added sodium metal (0.74 g). After heating under reflux for 4 hours under nitrogen, 2-chloro-6-trifluoromethyl pyridine in toluene was added and the whole treated under reflux for a further 8 hours. After conventional work-up and chromatography on silica/ether: hexane, 8-(6-trifluoromethyl-2'-pyridyloxy)-octan-1-ol was obtained.

The above alcohol was converted by the sequence as in Example 1 to give (2E,4E) N-isobutyl 12-(6-trifluoromethyl -2'-pyridyloxy)dodeca-2,4-dienamide. m.p. 89°.

EXAMPLES 4–35

The following compounds have been prepared:

TABLE 1

$$\text{(pyridine ring with X at position 4, O at position 2)} - O(CH_2)_m A(CH_2)_n(CE^1=CE^2)_a(CE^3=CE^4)CONR^1R^2$$

where A is —$CH_2$, $E^1$, $E^2$ and $E^4$ are hydrogen, a=1 and $R^1$ is hydrogen.

| Example No. | X | m + n | $E^3$ | $R^2$ | Prepared by analogy with Example No. |
|---|---|---|---|---|---|
| 4 | 6-$CF_3$ | 6 | H | sec.butyl | 3 |
| 5 | 4-$CF_3$ | 6 | H | $Bu^i$ | 3 |
| 6 | 5-$CF_3$ | 6 | H | $Bu^i$ | 3 |
| 7 | 3-$CF_3$ | 6 | H | $Bu^i$ | 3 |
| 8 | 6-$CF_3$ | 6 | Me | $Bu^i$ | 3 |
| 9 | 6-Cl | 6 | Me | $Bu^i$ | 3 |
| 10 | 6-Cl,4-$CF_3$ | 6 | H | $Bu^i$ | 3 |
| 11 | 6-Cl,4-$CF_3$ | 6 | Me | $Bu^i$ | 3 |
| 12 | 3-Cl | 6 | H | $Bu^i$ | 3 |
| 13 | 3-Cl | 6 | Me | sec.butyl | 3 |
| 14 | 6-Cl | 4 | H | $Bu^i$ | 1 |
| 15 | H | 6 | H | $Bu^i$ | 1 |
| 16 | H | 6 | H | sec.butyl | 1 |
| 17 | 5-Cl | 6 | H | $Bu^i$ | 3 |
| 18 | 5-Cl | 6 | Me | $Bu^i$ | 3 |
| 19 | 4,6-$(CF_3)_2$ | 6 | H | $Bu^1$ | 3 |
| 20 | 3,6-$(CF_3)_2$ | 6 | H | $Bu^i$ | 3 |
| 21 | 4,6-$(CF_3)_2$ | 6 | H | 2-methyl-prop-2-enyl | 3 |
| 22 | 4,6-$(CF_3)_2$ | 6 | H | (2-methyl-1,3-dioxalan-2-yl methyl- | 3 |
| 23 | 4,6-$(CF_3)_2$ | 6 | Me | $Bu^i$ | 3 |
| 24 | 5-Cl | 6 | H | 1,2-dimethyl-propyl | 1 |
| 25 | 5-Cl | 6 | H | $Bu^i$ | 1 |
| 26 | 2-Cl | 6 | Me | $Bu^i$ | 1 |
| 27 | 2-Cl | 6 | Me | 1,2-dimethyl-propyl | 1 |
| 28 | 2-Br | 6 | H | $Bu^i$ | 1 |
| 29 | 2-Br | 6 | Me | $Bu^i$ | 1 |

N.B. "$Bu^i$" is used to denote isobutyl

TABLE 2

$$\text{(pyrimidine ring)} - O(CH_2)_m A(CH_2)_n(CE^1=CE^2)_a(CE^3=CE^4)CONR^1R^2$$

where A, a, $E^1$, $E^2$, $E^4$ and $R^1$ are as defined above for Examples 4–23

3 $R^2$

The compounds of Examples 30 to 35 were prepared by analogous methods to those used previously:

EXAMPLE 30

(2E,4E) -N-( 1-methylpropyl ) 12-(4'-pyridyloxy)-dodeca-2, 4-dienamide

EXAMPLE 31

(2E,4E) N-Isobutyl 12-(4'-pyridyloxy)-dodeca-2,4-dienamide

EXAMPLE 32

A mixture of:
(2E,4E) N-Isobutyl 12-(4'-chloro-2'-pyrimidyloxy)-dodeca-2,4-dienamide and
(2E,4E) N-Isobutyl 12-(2'-chloro-4-pyrimidyloxy)-dodeca-2,4-dienamide

EXAMPLE 33

A mixture of:
(2E/Z,4E) N-Isobutyl 3-methyl-12-(4-chloro-2'-pyrimidyloxy) -dodeca-2,4-dienamide and
(2E/Z,4E) N-Isobutyl 3-methyl-12-(2-chloro-4'-pyrimidyloxy) -dodeca-2,4-dienamide

EXAMPLE 34

A mixture of:
(2E,4E) N-1-Methylpropyl 12-(4'-chloro-2-pyrimidyloxy) dodeca-2,4-dienamide and
(2E,4E) N-1-Methylpropyl 12-(2-chloro-4'-pyrimidyloxy) -dodeca-2,4-dienamide

EXAMPLE 35

(2E,4E) N-Isobutyl 12-(2',6'-bistrifluoromethyl-4'-pyridyloxy)-dodeca -2,4-dienamide

EXAMPLE 36

(2E,4E) N-Isobutyl 11-(6'-chloro-2'-pyridylmethoxy) -3-methylundeca-2,4-dienamide 6-Chloro-2-methylpyridine (20 g), (Ex Aldrich), N-bromosuccinimide (31 g), benzoyl peroxide ( 570 mg) and tetrachloromethane (250 ml) were heated together under reflux and under irradiation from a powerful lamp for 6 hours. After standard work-up and purification by column chromatography (silica; 5% ether in hexane), 6-chloro-2-bromomethylpyridine (25 g) was obtained.

Sodium hydride (0.109 mol.) was added to 1,7-heptanediol (0.218 mol.) in toluene. After heating under reflux for 3 hours, dry tetrahydrofuran was added, followed by 6-chloro-2-bromomethylpyridine (0.073 mol).

After heating under reflux for 4 hours, the cooled mixture was worked-up and purified by column chromatography (silica; 1:1 ether: hexane) to give 7-(6-chloro -2-pyridylmethoxy)-heptan-1-ol (12 g).

The above material was subjected to oxidation, reaction with 3-methyl triethylphosphonocrotonate and amidation with isobutylamine/trimethylaluminium as in Example 1.

The crude amide was purified by preparative HPLC (silica; 25% ethyl acetate, 75% hexane) to give (2E,4E) N-Isobutyl 3-methyl-11-(6-chloro-2-pyridylmethoxy)-undeca-2,4-dienamide as a colourless oil. NMR 7.2–7.7 (3H), m, pyridyl; 6.03 (2H),m,H4,5; 5.63 (1H),s,H2; 5.55 (Z) ethyl 4-bromo-2-fluoro-3-methylbut-2-enoates (4 g) which was heated under reflux in a Vigreux flask with triethylphosphite (3.8 g, 23.07 mmol) at 140°–150°. After 2 hours the crude product was purified by bulb to bulb distillation to give triethyl 2-fluoro -3-methyl-4-phosphonocrotonate (3.5 g, bp 160°–70° at 0.5 mm).

(ii) Sodium metal (90 mg) was added to 1,8-octanediol (2.2 g) in dry toluene (30 ml) at 100°. The whole was heated under reflux until all the sodium had been consumed and 2-chloro-3,5-bistrifluoromethylpyridine (ex Ishihara - Sanyo Inc.) in dry toluene (20 ml) was added. After heating under reflux for circa 5 hours the reaction mixture was worked up in conventional fashion and the crude product purified by column chromatography on silica (ether/hexane) to give 8-(3,5-bistrifluoromethyl-2-pyridyloxy)octan-1-ol (3 g).

The above alcohol (0.6 g) was oxidised under Swern conditions (dimethyl sulphoxide (0.26 g) oxalyl chloride (160 μl), triethylamine (1.0 ml)) in dichloromethane (30 ml) to give 8-(3,5-bistrifluoromethyl-2-pyridyloxy)octan-1-al. This was used directly in the next stage.

(iii) A solution of lithium diisopropylamide in dry tetrahydrofuran, prepared from diisopropylamine (0.3 ml) and n-butyl lithium (1.25 ml at 1.6M), was treated at −60° with triethyl 2-fluoro-3-methyl-4-phosphonocrotonate (471 mg) in tetrahydrofuran under nitrogen. The temperature was allowed to reach −10° and then recooled to −40° whereupon the above aldehyde was added. The reaction was maintained at 5° for 16 hours and worked up in conventional fashion. Chromatography on silica (4:1 hexane:ether) gave (2Z, 4E) ethyl 2-fluoro-3-methyl-12-(3,5-bistrifluoromethyl-2-pyridyloxy)-dodeca-2,4-dienoate.

(iv) The above ester (0.48 g) in dry toluene (2.5 ml) was added at −10° to a complex prepared from trimethylaluminium in toluene (700 μl at 1M) and redistilled isobutylamine (140 μl) in toluene (3.5 ml). After heating under reflux for 5 hours the reaction mixture was allowed to cool, treated with 2N hydrochloric acid and stirred for 30 mins. Dilution with ether and conventional work up gave a crude produce which was purified by flash column chromatography on silica (1:1 ether:hexane) to give the title compound as a pale yellow oil (0.3 g).

EXAMPLE 39

(2Z,4E)N-Isobutyl 2-fluoro-3-methyl-12-(3-chloro-5-trifluoromethyl-2-pyridyloxy) dodeca-2,4-dienamide Prepared by analogy with example 38 except that 2,3-dichloro-5-trifluoromethylpyridine (ex, Ishihara—Sanyo Inc.) was used in step (ii).

Physical-Chemical Data

TABLE 3

| Example No. | Melting point |
|---|---|
| 2 | 80–1° |
| 3 | 89° |
| 4 | 92° |
| 5 | 105° |
| 6 | 118° |
| 7 | 91–2° |
| 10 | 94° |
| 12 | 76–7° |
| 14 | 90–4° |
| 15 | 69–70° |
| 16 | 62–4° |
| 17 | 86° |
| 19 | 86° |
| 20 | 93–4° |
| 21 | 84° |
| 22 | 76° |
| 24 | 75° |
| 25 | 79–82° |
| 30 | 60–3° |
| 31 | 50–5° |
| 32 | 74° |
| 34 | 60–4° |
| 35 | 99° |

The compound of Example 8 had the following nmr spectrum:

(4:1,2E:2Z) 7.2(1H,t),7.23(1H,d), 6.88(1H,d), aromatic pyridyl; 6.04(m),7.55(d),(2H),H4,H5; 5.58(s),5.49(s), (1H),H2; 5.43(bd.s),NH; 4.32(2H,t),H12; 2.16(2H,m),H6;1.8 (2H,m)H11; 1.5(8H,m),methylene chain; 2.27(s),1.93(s), (3H),Me, (in ratio of 4:1); 3.23(2H,t),1.8(1H,m),0.92 (3H,s) isobutyl.

TABLE 4

| Example No. | R$_f$(silica/ether) | n$_d$ (18°) |
|---|---|---|
| 8 | 0.57 | |
| 9 | 0.57 | |
| 11 | | 1.36 |
| 13 | 0.63 | 1.547 |
| 18 | 0.23[1] | |
| 23 | | 1.374 |
| 26 | 0.38 | 1.549 |
| 27 | 0.38 | 1.547 |
| 28 | 0.21[1] | |
| 29 | 0.38 | |
| 33 | | 1.546 |
| 36 | 0.23[2] | |
| 37 | 0.62 | |
| 38 | 0.30 | |
| 39 | 0.50 | |

[1]1:1 ether/hexane
[2]6:4 hexane/ethyl acetate
[3]1:4 ether/hexane
[4]ether

All the halopyridines and hydroxypyridines are commercially available and were obtained from one or other of; Aldrich Chemical Co. Ltd., Lancaster Synthesis and Ishihara-Sanyo Inc.

Biological Activity

Example A

The compound of Example 1 was administered in acetone-water (5:95) by track-spray to a range of insect and acarine species, giving the following results.

| | |
|---|---|
| M. domestica | $LD_{50}$ about 200 ppm |
| S. granarius | $LD_{50} > 1000$ ppm |
| T. castaneum | $LD_{50} > 1000$ ppm |
| A. aegypti (larvae) | $LD_{50} > 1000$ ppm |
| C. quinquefasciatus | $LD_{50} > 1000$ ppm |
| P. xylostella (larvae) | 1000 ppm $> LD_{50} > 200$ ppm |
| M. persicae | 1000 ppm $> LD_{50} > 200$ ppm |
| T. urticae | 1000 ppm $> LD_{50} > 200$ ppm |

Example B

The compound of Example 1 and piperonyl butoxide (3 ul) were co-administered in cellosolve (2-ethoxyethanol) to female *M. domestica* topically. The $LD_{50}$ was between 0.3 and 0.06 mg/insect.

Example C

The compounds of the invention were tested by dissolving them in acetone (5%) and then diluting in water/'Synperonic' (94.5%/0.5%) to give a water emulsion. ("Synperonic" is a R.T.M. of I.C.I. plc and is nonylphenol ethoxylate in aqueous solution to give 27%; available from B.D.H., Poole, Dorset, England). The solution was then used to treat the following insects.

*Musca domestica*

20 female Musca were contained in a cardboard cylinder with gauze over either end. Solution containing the compound was sprayed onto the insects so enclosed and mortality assessed after 2 days at 25° C.

Examples 6, 8, 9, 10, 11, 16, 18, 23, 35, 38 were active at 1000 ppm and
Examples 1, 3, 4, 17, 19, 21, 22 were active at 200 ppm.

*Sitophilus granarius; Tribolium castaneum*

20 adult Sitophilus and Tribolium were added to 10 g wheat which had been previously treated with 2 ml of the solution containing the compound. Mortality was assessed after 6 days at 25° C.

*S. granarius*

Examples 10, 19, 21, 22, 31, 35 were active at 0.000 ppm

*T. castaneum*

Example 17 was active at 1000 ppm

*Plutella xylostella*

7 Fourth instar Plutella larvae were sprayed with the solution containing the compound and added to a chinese cabbage leaf which had been similarly sprayed and left to dry. Mortality was assessed after 2 days at 25° C.

Examples 1, 7, 11, 18, 24 were active at 1000 ppm and Examples 8, 9, 17 were active at 200 ppm Example 38 was active at 40 ppm.

or Discs of chinese cabbage infested with c8 second instar Plutella larvae were sprayed with the solution containing the compound. Mortality was assessed after 2 days at 25° C.

Example 36 was active at 1000 ppm and Examples 19, 20, 35 were active at 200 ppm.

*Myzus persicae*

10 adult Myzus were placed on a leaf disc of chinese cabbage. 24 hours later the disc was sprayed with the solution containing the compound. Mortality was assessed after 2 days at 25° C.

Examples 12, 14, 18, 30, 31, 33 were active at 1000 ppm and Examples 1, 13, 15, 16 were active at 200 ppm.

*Tetranychus urticae*

Leaf discs of infested french bean were sprayed with the solution containing the compound. Mortality was assessed after 2 days at 25° C.

Examples 1, 3, 4, 11, 17, 18, 21, 23, 27, 28, 29, 32, 34, 36 were active at 1000 ppm and Examples 8, 9, 25, 38 were active at 200 ppm.

*Spodoptera littoralis*

Uninfested leaves were sprayed with the test solution containing the compound (+pip but) and left to dry. These were then infested with 10 newly hatched larvae. Mortality was assessed after 3 days.

Example 38 was active at 200 ppm.

*Diabrotica undecimpunctata*

2nd instar larvae and their food were sprayed on filter paper with the solution containing the compound. Activity was assessed at 2 days.

Example 38 was active at 1000 ppm

Example D

The compounds of the invention were also tested by dissolving them in DMSO/acetone (50:50) to give a 5% solution, 1.0 ul of which was injected into fifth instar *Spodoptera littoralis* larvae. Mortality was assessed after 2 days at 25° C.

Examples 7, 8, 11, 29, 35 were active.

*Blatella germanica*

Examples 38 and 39 were active at up to 10 $\mu$g per insect (+piperonyl butoxide).

| Formulations | |
|---|---|
| 1. Emulsifiable Concentrate | |
| Compound of Example 1 | 10.00 |
| Ethylan KEO | 20.00 |
| Xylene | 67.50 |
| Butylated Hydroxyanisole | 2.50 |
| | 100.00 |
| 2. Wettable Powder | |
| Compound of Example 1 | 25.0 |
| Attapulgite | 69.50 |
| Sodium isopropylbenzene sulphonate | 0.50 |
| Sodium salt of condensed naphthalene sulphonic acid | 2.50 |
| Butylated hydroxytoluene | 2.50 |
| | 100.00 |
| 3. Dust | |
| Compound of Example 1 | 0.50 |
| Butylated Hydroxyanisole | 0.10 |
| Talc | 99.40 |
| | 100.00 |
| 4. Bait | |
| Compound of Example 1 | 40.25 |
| Icing Sugar | 99.65 |
| Butylated hydroxy toluene | 0.10 |
| | 100.00 |
| 5. Lacquer | |
| Compound of Example 1 | 2.5 |
| Resin | 5.0 |

| Formulations | |
|---|---|
| Butylated Hydroxy anisole | 0.5 |
| High aromatic white spirit | 92.0 |
| | 100.00 |
| 6. Aerosol | |
| Compound of Example 1 | 0.30 |
| Butylated Hydroxy anisole | 0.10 |
| 1,1,1-Trichloroethane | 4.00 |
| Odourless Kerosene | 15.60 |
| Arcton 11/12. 50:50 mix | 80.00 |
| | 100.00 |
| 7. Spray | |
| Compound of Example 1 | 0.1 |
| Butylated Hydroxy anisole | 0.1 |
| Xylene | 10.0 |
| Odourless Kerosene | 89.8 |
| | 100.00 |
| 8. Potentiated Spray | |
| Compound of Example 1 | 0.1 |
| Permethrin | 0.1 |
| Butylated Hydroxyanisole | 0.1 |
| Xylene | 10.1 |
| Odourless Kerosene | 89.8 |
| | 100.00 |

I claim:

1. A compound of the formula or a salt thereof:

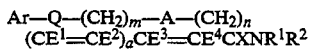
$(CE^1=CE^2)_aCE^3=CE^4CXNR^1R^2$ where Ar is a pyridyl ring attached at the 2, 3 or 4 position and is optionally substituted by one or more of halogen, cyano, $C_{1-6}$ alkyl, $C_{1-6}$ alkyl substituted by halogen, $C_{1-6}$ alkoxy, $C_{1-6}$ alkoxy substituted by one or more of halogen or $C_{1-6}$ alkyl, or $RS(O)_x$ where x is 0, 1 or 2 and R is $C_{1-6}$ alkyl optionally substituted by one or more halogen atoms, Q is $-CH_2-$ or $-O-$, m and n are each independently 0 to 7 and the total of m+n is 6 or greater, A is $-CH_2-$ or $-O-$, a is 1, $E^1$ to $E^4$ are independently hydrogen, $C_{1-4}$ alkyl, halo $C_{1-4}$ alkyl or halogen, X is oxygen or sulfur, and $R^1$ and $R^2$ are independently hydrogen, $C_{1-6}$ alkyl or $C_{3-6}$ cycloalkyl, either being optionally substituted by one or more of $C_{1-6}$ alkyl, $C_{2-6}$ alkenyl, dioxala- nyl, $C_{3-6}$ cycloalkyl, $C_{1-6}$ alkoxy or $RS(O)_x$- as defined above, provided that when Q and A are both $-O-$ m is at least 3.

2. A compound according to claim 1 wherein Ar is optionally substituted 2-pyridyl or 4-pyridyl.

3. A compound according to claim 2 wherein Ar is 2-pyridyl or 4-pyridyl substituted by one or more halo, trifluoromethyl or trifluoromethylthio groups.

4. A compound according to claim 1 wherein Q is $-O-$.

5. A compound according to claim 1 wherein A is $-CH_2-$ and the sum of m and n is even.

6. A compound according to claim 1 wherein each double bond conjugated to the amide carbonyl is trans.

7. A compound according to claim 1 wherein $E^1$ and $E^2$, are hydrogen, $E^3$ is hydrogen or methyl and $E^4$ is hydrogen.

8. A compound according to claim 1 where X is oxygen.

9. A compound according to claim 1 wherein Ar is optionally substituted by one or more of halogen, cyano, $C_{1-6}$-alkoxy (optionally substituted by one or more halogen) or $C_{1-6}$-alkoxy (optionally substituted by one or more of halogen (or $C_{1-6}$-alkyl), $E^1$ to $E^4$ are each independently hydrogen, $C_{1-4}$-alkyl or halo-$C_{1-4}$-alkyl, X is oxygen and $R^1$ and $R^2$ are independently hydrogen, $C_{1-6}$ alkyl or $C_{3-6}$-cycloalkyl, either being optionally substituted by one or more of $C_{1-6}$-alkyl, $C_{2-6}$-alkenyl, dioxalanyl and $C_{3-6}$-cycloalkyl.

10. A compound according to claim 1 where $R^1$ is hydrogen and $R^2$ is isobutyl, 1,2-dimethylpropyl, 2,2-dimethylpropyl, 1-methylpropyl (2-methyl-1,3-dioxalan-2-yl)methyl, or 1,1,2-trimethyl-propyl.

11. (2E,4E)N-isobutyl 12-(6'-chloro-2'pyridyloxy)-dodeca-2,4-dienamide; (2E,4E)N-isobutyl 3-methyl-12-(6'-trifluoromethyl -2'-pyridyloxy)dodeca-2,4-dienamide; (2E,4E) N-isobutyl 12-(4',6'-bistrifluoromethyl-2-pyridyloxy) -dodeca-2,4-dienamide; or (2E,4E) N-(2-methyl -1,3-dioxalan- 2-yl)-methyl 12-(4',6'-bistrifluoromethyl -2'-pyridyloxy)- dodeca-2,4-dienamide.

12. The compound of ((2E,4E)N-isobutyl 12-(4,6-trifluoromethyl-2-pyridoxy)dodeca-2,4-dienamide).

13. A pesticidal composition comprising a compound according to claim 1 and one or more carriers, diluents or solvents.

14. A method of combatting a pest by applying to the pest or its locus a composition according to claim 11.

* * * * *